US006955075B2

(12) United States Patent  
Carlson et al.

(10) Patent No.: US 6,955,075 B2  
(45) Date of Patent: Oct. 18, 2005

(54) PORTABLE LIQUID COLLECTION ELECTROSTATIC PRECIPITATOR

(75) Inventors: Duane C. Carlson, N. Augusta, SC (US); John J. DeGange, Aiken, SC (US); Justin E. Halverson, Grovetown, GA (US)

(73) Assignee: Westinghouse Savannah River Co., LLC, Aiken, SC (US)

( * ) Notice: Subject to any disclaimer, the term of this patent is extended or adjusted under 35 U.S.C. 154(b) by 0 days.

(21) Appl. No.: 10/287,409

(22) Filed: Nov. 4, 2002

(65) Prior Publication Data

US 2004/0083790 A1    May 6, 2004

(51) Int. Cl.$^7$ ............................................. G01N 37/00
(52) U.S. Cl. ................................................... 73/28.02
(58) Field of Search ........................... 73/28.02, 28.01; 95/75

(56) References Cited

U.S. PATENT DOCUMENTS

| | | | | |
|---|---|---|---|---|
| 3,315,445 A | | 4/1967 | DeSeversky | 55/122 |
| 3,444,667 A | * | 5/1969 | Mullin | 96/39 |
| 3,818,678 A | * | 6/1974 | Gothard | 95/75 |
| 3,917,470 A | * | 11/1975 | Xmris et al. | 96/80 |
| 4,074,983 A | * | 2/1978 | Bakke | 96/48 |
| 4,110,086 A | | 8/1978 | Schwab et al. | 55/7 |
| 4,216,000 A | * | 8/1980 | Kofoid | 96/80 |
| 4,308,038 A | * | 12/1981 | Michel | 96/47 |
| 4,360,366 A | | 11/1982 | Collins et al. | 55/119 |
| 4,362,538 A | | 12/1982 | Cox et al. | 55/118 |
| 4,373,937 A | | 2/1983 | Krause | 55/118 |
| 4,441,897 A | | 4/1984 | Young | 55/112 |
| 4,533,368 A | | 8/1985 | Snaddon | 55/104 |
| 4,654,054 A | | 3/1987 | Snaddon | 55/131 |
| 4,702,893 A | | 10/1987 | Kirk | 422/173 |
| 4,713,092 A | | 12/1987 | Kikuchi | 55/130 |
| 4,908,047 A | * | 3/1990 | Leonard | 95/71 |
| 5,003,774 A | * | 4/1991 | Leonard | 96/52 |
| 5,039,318 A | | 8/1991 | Johansson | 55/135 |
| 5,068,811 A | | 11/1991 | Johnston | 364/551 |
| 5,125,230 A | * | 6/1992 | Leonard | 60/274 |
| 5,137,546 A | | 8/1992 | Steinbacher et al. | 55/10 |
| 5,173,264 A | | 12/1992 | Zaromb et al. | 422/88 |
| 5,173,662 A | | 12/1992 | Trerice | 324/642 |
| 5,211,679 A | | 5/1993 | Meyer | 73/863 |
| 5,254,155 A | | 10/1993 | Mensi | 96/44 |
| 5,282,891 A | | 2/1994 | Durham | 96/75 |
| 5,328,851 A | | 7/1994 | Zaromb | 436/178 |
| 5,474,600 A | | 12/1995 | Volodina | 98/57 |
| 5,526,110 A | | 6/1996 | Braymen | 350/316 |
| 5,601,791 A | | 2/1997 | Plaks et al. | 422/169 |
| 5,707,428 A | | 1/1998 | Feldman | 96/54 |

(Continued)

Primary Examiner—Hezron Williams  
Assistant Examiner—Rodney Frank  
(74) Attorney, Agent, or Firm—McNair Law Firm, P.A.

(57) ABSTRACT

A portable liquid collection electrostatic collection precipitator for analyzing air is provided which is a relatively small, self-contained device. The device has a tubular collection electrode, a reservoir for a liquid, and a pump. The pump pumps the liquid into the collection electrode such that the liquid flows down the exterior of the collection electrode and is recirculated to the reservoir. An air intake is provided such that air to be analyzed flows through an ionization section to ionize analytes in the air, and then flows near the collection electrode where ionized analytes are collected. A portable power source is connected to the air intake and the collection electrode. Ionizable constituents in the air are ionized, attracted to the collection electrode, and precipitated in the liquid. The precipitator may also have an analyzer for the liquid and may have a transceiver allowing remote operation and data collection.

11 Claims, 3 Drawing Sheets

U.S. PATENT DOCUMENTS

| | | |
|---|---|---|
| 5,753,012 A | 5/1998 | Firnhaber et al. ............... 95/65 |
| 5,792,238 A | 8/1998 | Johnson et al. ................ 95/60 |
| RE35,990 E * | 12/1998 | Greene et al. .............. 110/345 |
| 5,846,301 A | 12/1998 | Johnson et al. ................ 96/52 |
| 5,892,141 A | 4/1999 | Jones et al. ................ 73/24.03 |
| 5,922,111 A | 7/1999 | Omi ............................... 96/60 |
| 5,993,521 A | 11/1999 | Loreth ............................ 96/69 |
| 6,087,183 A | 7/2000 | Zaromb ...................... 436/178 |
| 6,106,592 A | 8/2000 | Paranjpem et al. ............ 95/65 |
| 6,153,168 A | 11/2000 | Seitz et al. .................. 423/522 |
| 6,156,098 A | 12/2000 | Richards ........................ 95/65 |
| 6,221,136 B1 | 4/2001 | Liu et al. ....................... 96/66 |
| 6,248,217 B1 * | 6/2001 | Biswas et al. ............ 204/157.4 |
| 6,294,003 B1 | 9/2001 | Ray .............................. 96/49 |
| 6,364,941 B2 | 4/2002 | Liu ............................... 96/60 |
| 6,488,740 B1 * | 12/2002 | Patel et al. .................... 95/71 |
| 6,508,861 B1 * | 1/2003 | Ray ............................... 95/79 |
| 6,520,034 B1 | 2/2003 | Masquelier et al. |

\* cited by examiner

PORTABLE LIQUID COLLECTION ELECTROSTATIC PRECIPITATOR

STATEMENT OF GOVERNMENT RIGHTS

The United States Government has rights in this invention pursuant to Contract No. DE-AC09-96SR18500 between the U.S. Department of Energy and Westinghouse Savannah River Company.

FIELD OF THE INVENTION

This invention relates to electrostatic precipitators having wetted collection electrodes, and more particularly to portable electrostatic precipitators. The current invention is directed to a portable liquid collection electrostatic precipitator capable of collecting analytes from air and concentrating the analytes in the liquid, and may include means allowing analysis of the collected analytes and means for remotely controlling the precipitator and communicating data to a remote location. The invention also relates to a method for obtaining and concentrating analytes from air, particularly at a remote location.

BACKGROUND OF THE INVENTION

Electrostatic precipitators, or collectors, are known to the art. In the simplest form, an electrostatic precipitator has a collection electrode that is electrostatically charged. Adjacent to or surrounding the collection electrode is another surface that can be electrostatically charged. The collection electrode and the adjacent or surrounding surface are oppositely charged by a power source, thereby creating an electrostatic field. As air and any constituents of the air move, actively or passively, into the electrostatic field, the ionizable constituents of the air are ionized. The ionizable constituents are attracted to and collect on the collection electrode.

There are two main types of electrostatic precipitators. Dry precipitators are essentially as described above. Constituents collected on the electrode must be periodically wiped off or otherwise removed from the electrode, or the electrode must be replaced. Wiping mechanisms may be used, or the precipitator must be periodically shut down for cleaning.

Wet or liquid electrostatic precipitators also make use of collection electrodes. In this type of precipitator, however, the collection electrode is periodically or continually washed with a liquid. In these types of precipitators, the collection electrodes are generally planar sheets or plates and are arranged vertically. A liquid such as water is conveyed along the upper edges of the sheets or plates such that it flows down the electrodes. The liquid serves to clean the collection electrode(s) on a continuous or periodic basis, avoiding the need to stop the operation of the precipitator to clean or replace electrodes. The liquid is typically conveyed to a disposal system where it can be filtered and otherwise cleaned.

There are numerous designs of the two types of precipitators briefly described above and known to the art. These precipitators are typically used in industrial and commercial applications to clean ventilation air in buildings of dust and other constituents, or to clean exhaust air from chemical and other manufacturing processes. To accomplish this, the precipitators are typically large structures to provide the greatest surface area possible for collection electrodes to increase the efficiency of the cleaning process. These structures require correspondingly large enclosures. Also, precipitators of this size for these purposes also require large amounts of electrical power to create and maintain the electrostatic fields.

For the foregoing reasons, electrostatic precipitators known to the art are limited to use in fixed locations. They are also limited to use at locations having space available for such apparatus, and at locations having sufficient resources, such as available power, for such use. These requirements also limit use of such precipitators to locations and to uses justifying the expenditures necessary to install, operate, and maintain such devices. Finally, precipitators known in the art are limited to specific uses such as cleaning air that is being taken in to a facility or air that is being exhausted from a facility.

The invention disclosed and claimed herein, while operating on the same principles as precipitators known in the art, presents an electrostatic precipitator that does not suffer from the limitations inherent in those described above and enables a method of sampling air at selected locations.

SUMMARY OF THE INVENTION

It is an object of this invention to provide a liquid collection electrostatic precipitator that is portable.

It is also an object of this invention to provide an electrostatic precipitator that is capable of collecting constituents or analytes from air at a selected location such that the analytes can be analyzed.

It is likewise an object of this invention to provide a precipitator that can easily be transported to a selected location, operated at that location, and transported again to a facility for analysis of analytes collected from the air at the selected location.

It is a further object of this invention to provide a portable electrostatic precipitator capable of concentrating analytes from air such that even minute amounts of analyte present at a collection location can be detected and analyzed.

It is another object of this invention to provide a liquid collection electrostatic precipitator that can be placed in a remote location and operated by an operator situated in a different location.

It is still another object of this invention to provide an electrostatic precipitator having at least one analyzer that can detect an analyte collected by the precipitator and provide data relating to the analyte.

It is also an object of this invention to provide a precipitator capable of collecting and analyzing at least one analyte from air and capable of transmitting data from the analysis to an operator at a remote location.

It is an object of this invention to provide a method of collecting and concentrating at least one analyte from air such that the analyte is collected in an amount sufficient to enable analysis of the analyte, and optionally to provide a transmitting means capable of transmitting data concerning the analyte to a location remote from the location of the air being analyzed.

These and other objects of the invention are realized by providing a portable liquid collection electrostatic precipitator having a vertical tubular collection electrode; a reservoir containing a liquid, the reservoir being hydraulically connected to the collection electrode; a pump for pumping the liquid from the reservoir to the interior of the collection electrode such that the liquid flows over the exterior of the collection electrode and is returned to the reservoir; an air intake positioned so as to allow air to flow near the exterior of the collection electrode; an ionization section within the air intake to ionize analytes in the air; and a portable power source operatively connected to the collection electrode and the ionization section respectively; whereby ionizable analytes of the air are electrostatically precipitated on the collection electrode and collected in the liquid.

These and other objects of the invention are also realized by providing a method for collecting and concentrating analytes in air at a selected location by providing a portable liquid collection electrostatic precipitator as described, operating the precipitator for a selected period of time such that analytes in the air are collected and concentrated in the recirculated liquid of the precipitator.

The objects of this invention are also realized by providing the described precipitator with additional components known to the art such as transceivers and analyzers such that the precipitator can be transported to a selected location, and operated by an operator by commands transmitted to and from the precipitator. One or more analyzers associated with or integrated into the precipitator can also be operatively connected to the transceiver such that the analyzer can be operated by remote control, and data from the analyzer can be transmitted via the transceiver to the operator, thus allowing analysis of air at the selected location in the absence of manual control of the precipitator.

DETAILED DESCRIPTION OF THE INVENTION

Figure 1:
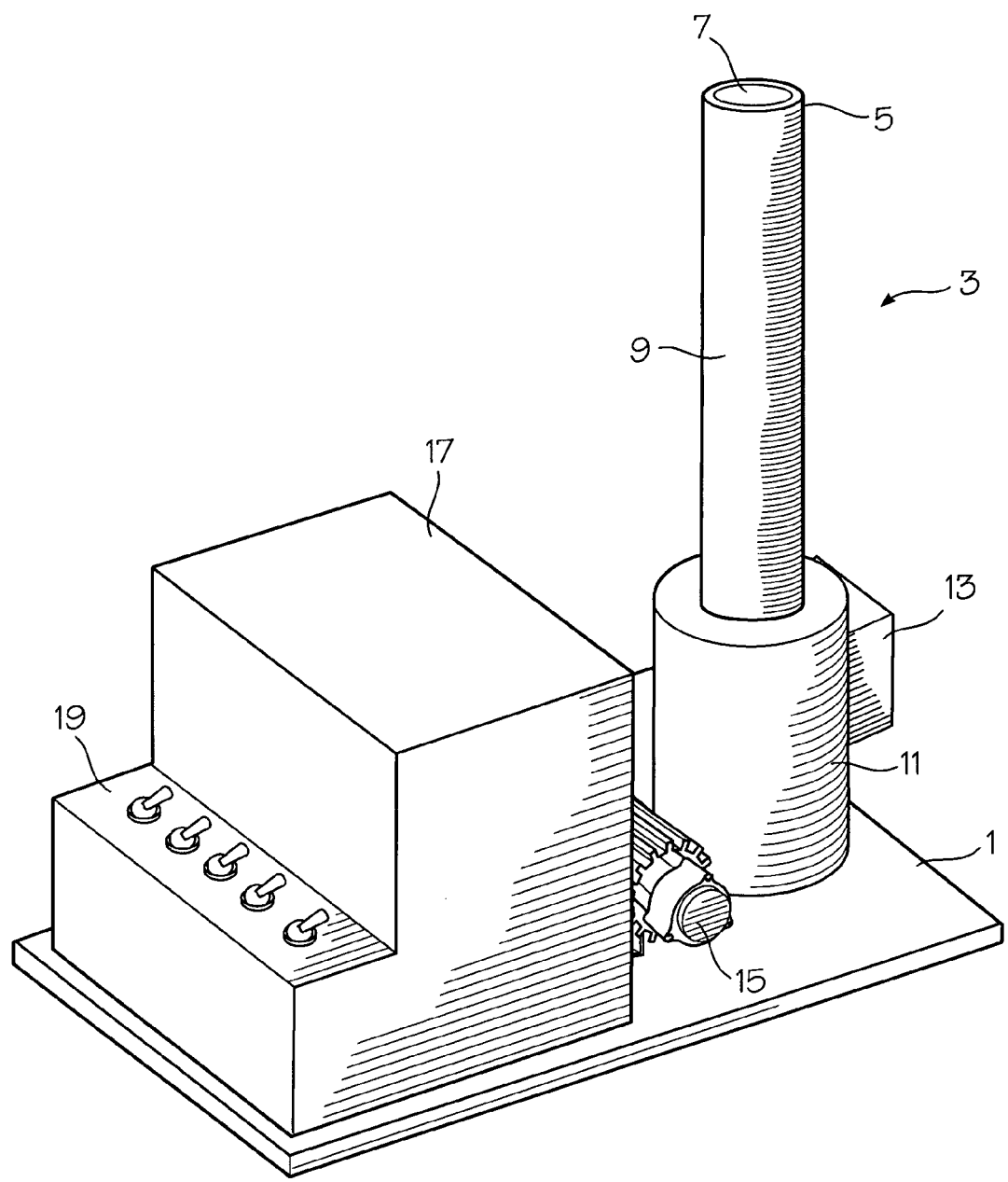
FIG. 1 is a diagrammatic illustration of a preferred embodiment of the portable electrostatic precipitator according to the current invention.

Electrostatic precipitators, as noted, are known in the art for the purpose of "scrubbing" air streams in commercial and industrial applications. To efficiently and thoroughly clean materials from air being introduced into a facility, such as offices, "clean rooms," or medical facilities, or to clean air being vented or exhausted from manufacturing facilities, the precipitators are required to provide high-voltage electrostatic fields and large surfaces for the collection electrodes. Reducing the rate at which air is passed through the precipitator is usually not an option, because the volume of air that must be processed per unit time is determined by the nature and size of the facility. Attention in this field has therefore generally been directed toward improving the efficiency of the precipitators by improving or manipulating the flow of air, enhancing the effective area of the collection electrodes, enhancing the effective strength of the electrostatic field, or other similar aspects of precipitators.

It is possible, in the use of precipitators as described for treating air streams, to analyze the content of the air being processed. Any portion of the air, such as gases, microbes (including any airborne microorganisms such as spores, bacteria, fungi, and the like), dust or any other particles that may be entrained in or carried by the air (hereafter referred to as "analytes") that can be ionized by the electrostatic field, can be collected on the collecting electrode and thereafter analyzed. In dry precipitators, the analytes can be periodically removed from the electrode and conveyed to an analyzer. In wet precipitators, the liquid used to wet the electrodes can similarly be conveyed to an analyzer for analysis. In existing precipitators, however, the air stream to be analyzed is limited to the air stream being treated at the facility.

The current invention takes advantage of the efficiencies of electrostatic precipitation in a portable, self-contained unit that enables the collection, concentration, and analysis of air-borne analytes in virtually any selected location. The unit can be transported easily to a selected location where collection or analysis of air-borne analytes is desired. The unit can be operated by an operator at the location, or can be provided with a communications device, such as a simple radio transceiver, allowing operation from a remote location.

In a preferred mode, the unit includes a portable power source which can, for example, be a standard 12-volt automobile battery. The unit can also be adapted to use an on-site power source, or can use any of a variety of specialized battery, including for example solar batteries or solar panels. The requirements for the power source for the precipitator are that it must (1) be capable of producing an electrostatic field of the desired intensity and (2) have sufficient additional power to operate other components of the unit, all of which will have relatively low power requirements. The portable power source provides all the power needed for the functions of the precipitator, and the exact requirements of power can easily be determined by those of skill in the art.

FIG. 1 shows, in diagrammatic fashion, some of the primary components of the apparatus according to the invention. There is provided a base 1 to which the other components may be mounted. Because in a preferred embodiment the entire unit is intended to be self-contained and portable, it is preferred that the components of the precipitator be securely attached to the base, and that the base is made of materials such as metal, plastic, or wood to provide durability and stability during transport and use.

Mounted on base 1 is an air intake system 3, described more fully below. The air intake system 3 is provided with an inlet end 5 having an air inlet 7, an air passage 9 depicted in FIG. 1 as a hollow tube, and an outlet end 11 for exhausting air. A fan or air pump 13 operates to draw air into the air inlet 7, through air passage 9 and out through outlet end 11, thus creating an air stream through the air intake system 3. Also mounted on base 1 is a fluid pump 15, described more fully below. An electronics module 17 is mounted on base 1, as is a control panel 19. Electronics module 17 and control panel 19 may comprise a single component of the precipitator apparatus.

Electronics module 17, in a preferred mode, consists of a power source (not shown) such as a battery. It also contains standard electronic circuitry as is known in the art for converting electronic power from the power source to operate the various components of the precipitator. The control panel 19 contains the controls for the various components of the precipitator. Electronics module 17 or control panel 19 may also incorporate a remote communications system (not shown) such as a radio transceiver, such that signals can be sent to and from the precipitator to allow remote control of the precipitator and remote access to data from the precipitator or components thereof, as will be described below.

Figure 2:
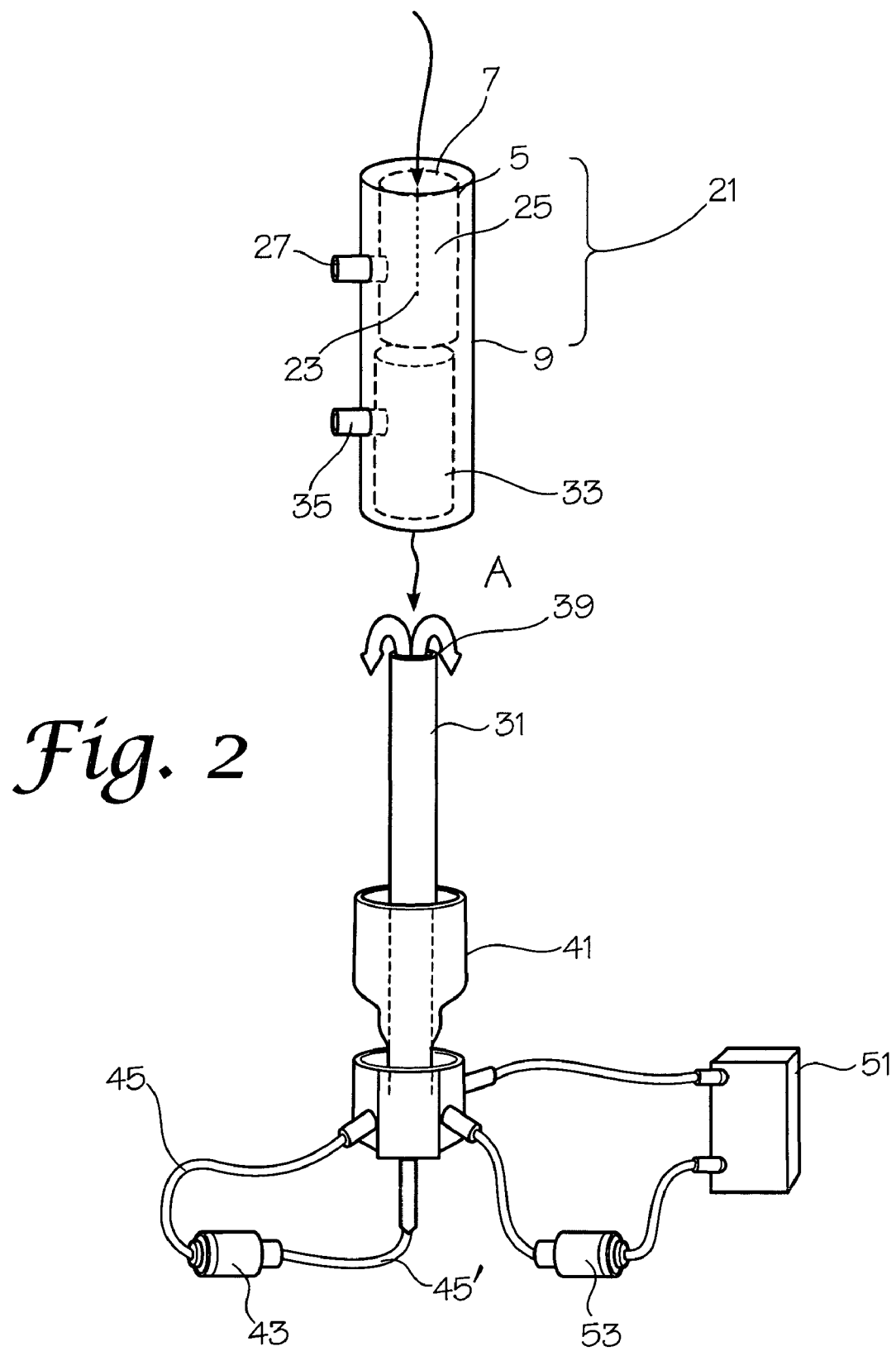
FIG. 2 is a more detailed, semi-exploded illustration of one embodiment of the invention showing certain details of the invention.

FIG. 2 is a diagrammatic depiction of certain components of the precipitator according to one preferred embodiment of the invention. To effect collection of analytes from air, air is drawn into air passage 9 through air intake 7 at the intake end 5 of the air intake system 3. Near air intake end 5 of air passage 9 is an ionization section 21. In the embodiment of the invention shown in FIG. 2, ionization section 21 consists of an ionization wire 23 suspended within air passage 9 near intake end 5. Ionization wire 23 is electrically connected to a source of high-voltage electricity (not shown in FIG. 2) such that wire 23 is charged at high voltage, preferably at about 8,000 to 9,000 volts. Located near ionization wire 23 is a wire ground plate 25, which may take the form of a tubular conductive material surrounding wire 23 and attached to air passage 9. Wire ground plate 25 is connected to ground through a connection 27.

A collection electrode 31 is mounted within air intake system 3, and particularly within air passage 9 such that the air stream flowing through air passage 9 flows in close proximity to collection electrode 31. Collection electrode 31 is a hollow tubular structure. It may be made of conductive material, or may comprise any selected material that is coated or otherwise treated to be electrically conductive. Collection electrode 31 is electrically connected to a source of high-voltage electrical power such that it is charged oppositely with respect to ionization wire 23. Analytes that are ionized in passing through ionization section 21 are therefore strongly attracted to collection electrode 31. A collection electrode ground plate 33 is also provided in air passage 9 and positioned to be adjacent collection electrode 31. A connection 35 connects collection electrode ground plate 33 to an electrical ground.

It can be seen from FIG. 2 that when air passage 9 is lowered in the direction of arrow A, the ionization section 21 will be above but closely adjacent to collection electrode 31. Air drawn through air intake 7 will pass through ionization section 21 and be directed around and adjacent to collection electrode 31. Ionizable analytes in the air stream will be ionized in ionization section 21 and collected on collection electrode 31 with a very high efficiency.

To collect analytes attracted to and precipitated on collection electrode 31, a reservoir containing a fluid is provided. As shown in the embodiment of FIG. 2, a reservoir 41 is provided at the base of collection electrode 31. Reservoir 41 is hydraulically connected to the interior of collection electrode 31, and a pump 43 and hydraulic connections 45, 45' are provided to pump the liquid. When pump 43 is activated, liquid in reservoir 41 is pumped to the hollow interior of collection electrode 31. Collection electrode 31 is provided with an open upper end 39. As liquid is pumped to the interior of collection electrode 31, it is expelled through open upper end 39 and cascades down the exterior of collection electrode 31 and is returned to reservoir 41. It is preferred that the liquid contain a surfactant such that the liquid is effectively distributed on the exterior of the collection electrode 31. As liquid flows down the exterior of collection electrode 31, analytes precipitated on collection electrode 31 are collected in the liquid.

In operation of the precipitator, air is drawn into air passage 9. Analytes in the air stream are ionized in ionization section 21 due to the high-voltage charge carried by ionization wire 23. The ionized analytes are then carried by the air stream to the vicinity of collection electrode 31, which carries a high-voltage charge, opposite in polarity to that carried by ionization wire 23. Ionized analytes are attracted to collection electrode 31 on which they precipitate. The analytes are then collected in the liquid being circulated to and from reservoir 41, whereby analytes are collected and concentrated in the liquid.

Air pump 5, liquid pump 43, and the power supply for ionization wire 23 and collection electrode 31 are provided by the power supply described above and controlled via the controls on control panel 19. The system may be operated for a selected period of time by an operator on-site, or may be operated remotely. The liquid can then be collected and analyzed.

The system according to the disclosed invention may also include one or more analyzers. As depicted diagrammatically in FIG. 2, an analyzer 51 can be mounted on base 1. Analyzer 51 is hydraulically connected to reservoir 41 such that liquid from reservoir 41 is circulated through analyzer 51. An analyzer pump 53 may be provided, or the liquid may be circulated through analyzer 51 through the action of liquid pump 43.

Figure 3:
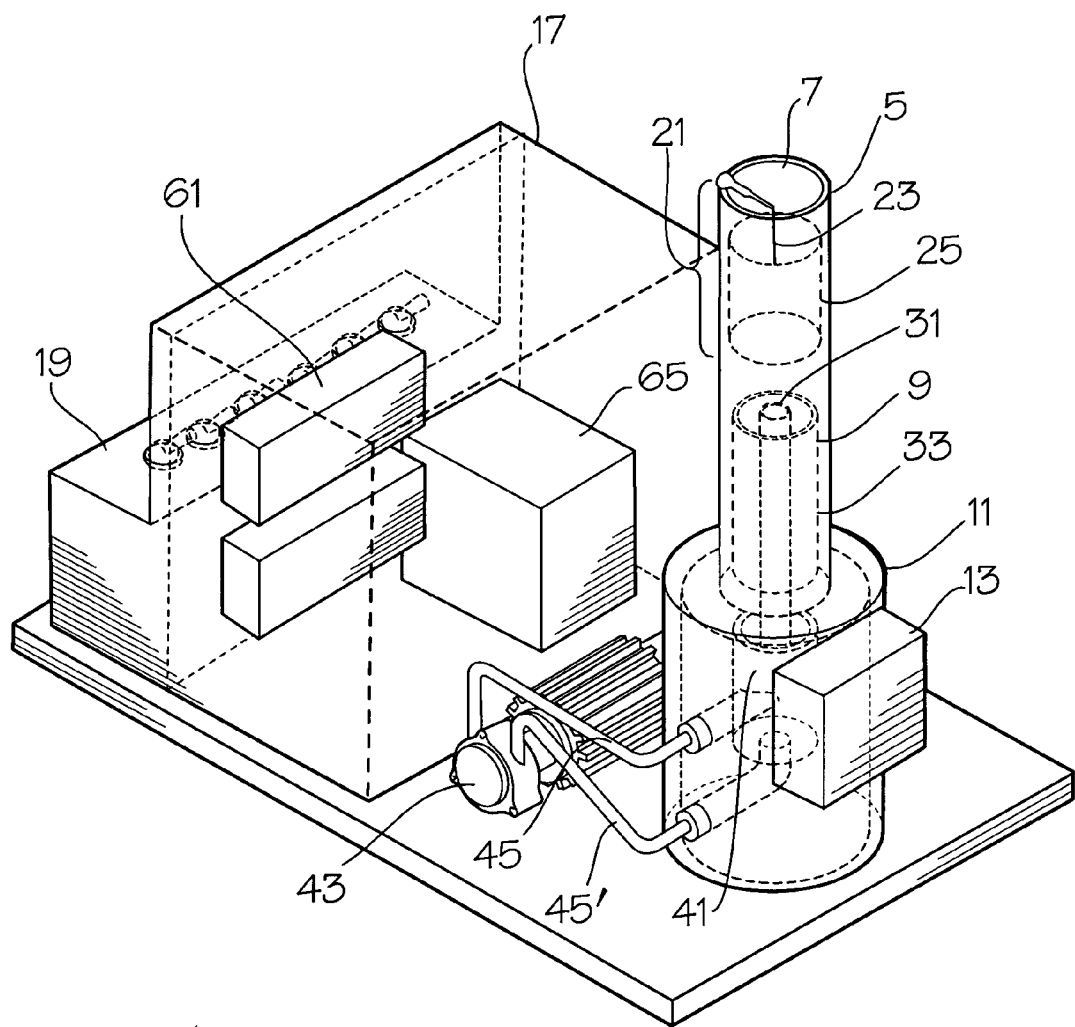
FIG. 3 is another diagrammatic illustration of a preferred embodiment of the invention.

FIG. 3 is another depiction of a portable liquid collection electrostatic precipitator according to the disclosed invention, illustrating a more fully assembled apparatus. Using like numbers to indicate like components, FIG. 3 shows air passage 9 having an air intake end 5 and air intake 7. Located near air intake end 5 is ionization section 21 having ionization wire 23 and wire ground plate 25. Located in air passage 9 between ionization section 21 and outlet end 11 is collection electrode 31 and collection electrode ground plate 33. Reservoir 41 containing a liquid (not shown) is hydraulically connected to the interior of collection electrode 31, and liquid is recirculated by a liquid pump 43. An electronics module 17 is shown, and depicted therein is an ionizer high voltage supply 61 for supplying voltage to ionization wire 23, a collector high voltage supply 63 for supplying voltage to collection electrode 31, and a pump power supply 65 for supplying power to liquid pump 43 and air pump 13.

The electrostatic precipitator disclosed herein has been shown to be highly effective in collecting airborne analytes. A prototype has been tested and has been shown to effectively collect spores of the bacterium *Bacillus thuringiensis*. The significance of this capability is that the spores of *B. thuringiensis* are approximately the same size as spores of various microbes that may be used as biological weapons, such as anthrax. Spores of this size are very difficult to collect by other methods, such as by the use of HEPA filters. Electrostatic precipitation can also be used to collect molecules and other substances associated with, for example, explosives. The current invention, through the use of recirculating liquid as described, can not only collect such analytes, but concentrates them in the liquid, allowing faster and/or more accurate analysis.

As described, one or more analyzers may be incorporated into the precipitator. The liquid used can also be adapted to one or more particular analytes such that the liquid constitutes a carrier suitable for use in the analyzer. While many examples can be described, a few illustrate some of the possibilities. The liquid used in the precipitator can include a scintillation cocktail such as is known in the art. An analyzer having a photodetector tube can then be used to determine activity in the cocktail, and can provide an output indicative of detected scintillation. A positive output would then indicate the presence of radioactive analytes. The liquid can alternatively include colorimetric materials, that is, materials that change color or color intensity upon exposure to certain analytes. An analyzer having a colorimetric cell can then provide data relating to the collection and/or concentration of analytes. The liquid can comprise a buffered saline solution or a nutrient solution such that biological materials that are collected will remain in a viable state, thereby making analyses of the material faster and more accurate. Those of skill in the art will be aware of other materials that may be included in the liquid, and other analyzers effective at detecting other types of analytes.

The apparatus according to the disclosed invention enables a method for collecting and concentrating analytes through the use of the portable electrostatic precipitator. The method consists of providing a precipitator according to the invention, locating the precipitator at a selected location, and operating the precipitator for a selected period of time, thereby collecting and concentrating airborne analytes. Because the precipitator can have its own power supply, it can be located at almost any desired location. The apparatus and method can be used for specific testing, or can be used as remote monitoring methods. Collection of airborne analytes may serve research functions, as by periodically sampling air in the selected location, or can be used to monitor for the presence of chemical, biological, and other hazardous materials.

The invention is subject to a number of variations. As described herein, a preferred embodiment of the invention utilizes a wire in the ionization section. Other means of creating an ionization field are known. Various materials emit particles such as α-particles or β-particles that can be used to directly or indirectly ionize airborne analytes. Radio frequency emitters known to those of skill in the art can also be used to ionize the analytes. Alternate power sources may be used, and other individual components of the precipitator may be changed in design. Such variations do not depart from the scope of the disclosed invention, which is to be measured by the following claims.

What is claimed is:

1. A portable liquid collection electrostatic precipitator comprising:

an air intake system, said system comprising an air passage having an inlet end and an outlet end and an air pump, said pump operative to draw air from said inlet end through said air passage and out through said outlet end, thereby creating an air stream through said air passage;

an ionization section located in said air intake system near said inlet end, said ionization section capable of ionizing analytes in said air stream;

a collection electrode situated in said air intake system between said ionization section and said outlet end of said air intake system whereby the exterior of said collection electrode is exposed to said air stream, said collection electrode comprising a vertical tubular electrode;

a reservoir containing a liquid, said reservoir hydraulically connected to said collection electrode;

a liquid pump for pumping said liquid from said reservoir to the interior of said collection electrode such that said liquid flows upwardly through the interior of the collection electrode and then flows downwardly over the exposed exterior of said collection electrode and is returned to said reservoir;

a portable power source, said power source operatively connected to said ionization section and said collection electrode to create an electrostatic field capable of ionizing analytes in said air;

whereby ionizable analytes in said air stream are electrostatically precipitated on said collection electrode and collected in said liquid.

2. The precipitator according to claim 1, wherein said air pump is capable of pumping air through said air intake system at a rate of about 300 liters/minute.

3. The precipitator according to claim 1, wherein said liquid comprises a nutrient mixture.

4. The precipitator according to claim 1, wherein said liquid comprises at least one indicator for at least one ionizable analyte of said air.

5. The precipitator according to claim 1, wherein said ionizer section comprises an ionization wire and a ground plate and wherein said portable power source is capable of creating an electrostatic charge on said ionization wire of about 8,000 to 9,000 volts.

6. The precipitator according to claim 1, wherein said liquid comprises at least one surfactant.

7. The precipitator according to claim 1, further comprising: a transceiver operatively connected to said power source whereby said precipitator can be remotely controlled.

8. The precipitator according to claim 7, further comprising:

an analyzer hydraulically connected to said reservoir whereby liquid in said reservoir is directed to said analyzer such that said analytes collected in said liquid can be analyzed, said analyzer also operatively connected to said transceiver such that data from said analyzer can be transmitted to a remote location.

9. A method for collecting and concentrating analytes from air, the method comprising:

providing a liquid collection electrostatic precipitator, said precipitator comprising:

an air intake system, said system comprising an air passage having an inlet end and an outlet end and an air pump, said pump operative to draw air from said inlet end through said air passage and out through said outlet end, thereby creating an air stream through said air passage;

an ionization section located in said air intake system near said inlet end, said ionization section capable of ionizing analytes in said air stream;

a collection electrode situated in said air intake system between said ionization section and said outlet end of said air intake system whereby the exterior of said collection electrode is exposed to said air stream, said collection electrode comprising a vertical tubular electrode;

a reservoir containing a liquid, said reservoir hydraulically connected to said collection electrode;

a liquid pump for pumping said liquid from said reservoir to the interior of said collection electrode such that said liquid flows upwardly through the interior of the collection electrode and then flows downwardly over the exposed exterior of said collection electrode and is returned to said reservoir;

a portable power source, said power source operatively connected to said ionization section and said collection electrode to create an electrostatic field capable of ionizing analytes in said air;

whereby ionizable analytes in said air stream are electrostatically precipitated on said collection electrode and collected in said liquid;

locating said precipitator at or near a selected location at which air is to be analyzed; and operating said precipitator for a selected period of time to collect analytes from said air stream by electrostatic precipitation of said analytes on said collection electrode and said liquid is re-circulated between said reservoir and said collection electrode during said selected period of time;

whereby analytes in said air stream are collected and concentrated in said liquid.

10. The method according to claim 9, wherein:

said precipitator further comprises a transceiver operatively connected to said power source, said transceiver capable of communicating with a remote location whereby an operator at said remote location can operate said electrostatic precipitator.

11. The method according to claim 10, wherein said precipitator further comprises an analyzer operatively connected to said reservoir, said analyzer capable of detecting at least one analyte collected and concentrated in said liquid; and wherein said transceiver is operatively connected to said analyzer whereby data from said analyzer can be transmitted to an operator at said remote location.

* * * * *